United States Patent [19]

Uehara

[11] 4,421,106
[45] Dec. 20, 1983

[54] FIBER SCOPE FOR BIOPSY OPERABLE BY A SINGLE OPERATOR

[76] Inventor: Takami Uehara, 1126, Hojo-1-chome, Daito-shi, Japan

[21] Appl. No.: 281,413

[22] Filed: Jul. 8, 1981

Related U.S. Application Data

[63] Continuation of Ser. No. 77,125, Sep. 19, 1979, abandoned, which is a continuation of Ser. No. 778,961, Mar. 18, 1977, abandoned.

[30] Foreign Application Priority Data

Mar. 19, 1976 [JP] Japan .................................. 51-30670

[51] Int. Cl.³ .............................................. A61B 1/00
[52] U.S. Cl. .................................................... 128/4
[58] Field of Search ...................... 128/4, 5, 6, 7, 311, 128/321, 751; 251/8, 9, 10

[56]  References Cited
U.S. PATENT DOCUMENTS 3,544,060  12/1970  Stoltz et al. .............................. 251/9

Primary Examiner—William E. Kamm
Assistant Examiner—Max F. Hindenburg
Attorney, Agent, or Firm—Armstrong, Nikaido, Marmelstein & Kubovcik

[57] ABSTRACT

A fiber scope for biopsical use which is designed to be operable by a single operator, and which comprises a pair of forceps with a relatively short extension, an adaptor for selectively controlling a motion of the forceps tip ends, and a stopper adapted to selectively fix the longitudinal motion of the forceps controlling wire with respect to the fiber scope proper. The adaptor is disposed at or adjacent to the inlet portion of a forceps guide sleeve which surrounds and extends longitudinally toward the tip end and operating handle of the forceps. The combination of the adaptor and the stopper will effectively serve to provide a delicate and versatile adjustment in positioning of the forceps with an easy manipulation during a biopsical investigation and sampling procedure.

3 Claims, 4 Drawing Figures

FIBER SCOPE FOR BIOPSY OPERABLE BY A SINGLE OPERATOR

This is a continuation of application Ser. No. 77,125, filed Sept. 19, 1979 which is a continuation of application Ser. No. 778,961 filed Mar. 18, 1977, both of which are now abandoned.

BACKGROUND OF THE INVENTION

The present invention relates in general to a biopsical fiber scope for medical biopsical examination purposes, or particularly to a biopsy fiber scope which is operable by a single operator for selective orientational control and delicate biopsy procedure in a living internal organ of a patient or a laboratory animal.

Recently, following the extensive improvement in medical technology, there have been developed and extensively practiced a variety of medical instruments for biopsical examinations which can be directly inserted into such internal organs as stomach, duodenum, colon, etc. of a patient or a laboratory animal and which have been adapted to observe and take a tissue sample of a designated part of the living internal organ. Some typical examples of such biopsical medical examination instruments are a fiber scope developed by Hirschowitz (phonetic) which comprises a bundle of optical fibers coated with a substance having a relatively small index of refraction on the outer circumference of a core having a relatively large index of refraction, and a biopsical fiber scope which was developed by Takagi et al. by combining a pair of forceps for biopsy use with that fiber scope as shown in FIG. 1. Another typical flexible fiber scope is shown in U.S. Pat. No. 3,897,775. These include a control unit housing with a branched conduit therein. A flexible hollow conduit is attached to the housing. An optic assembly is provided including an eyepiece assembly, a bundle of flexible optical fibers and an objective assembly to permit viewing of the area being examined.

Although such prior art fiber scopes presented an innovent practice in the field of biopsical medical examination on the living tissues, these biopsical fiber scopes are designed and constructed for use by an operator and at least one assistant during a medical examination in such a manner that while an operator proceeds with an examination of the interior tissues of the living organ by using a fiber scope, an assistant operates a forceps which is operatively connected to a trigger or the like disposed outside of the fiber scope, so as to take a tissue sample according to the instructions given by the operator.

In these instruments of such construction, it is essentially required that the operator and his assistant cooperate in harmony, which requires a well-prepared proficiency in the joint operation of a fiber scope, otherwise, an improper fiber scope operation would give pain or even a physical damage to a patient, and sometimes it was practicably difficult or even impossible to take a proper sample tissue quickly and correctly at the focal point which is being observed and targetted at by the operator. Such problems as experienced in the operation of the prior art fiber scopes are more or less attributable to the manner of operation which requires more than one operator, thus they have been very inconvenient to handle.

It would be advantageous in this consideration, if an improved biopsical fiber scope operable by a single operator for a proper biopsy operation is made available, which would overcome all such drawbacks as experienced in the prior art fiber scope and which still unsolved until now. In order to meet the above mentioned problems, it is deemed to be highly desirable to provide an improved medical instrument for biopsical examination which is operable freely for carrying out an orientational control and a series of biopsical manipulations by a single operator. For such purpose, it is essential to provide an improved biopsy fiber scope of such construction that there is provided a pair of forceps having a relatively short extension in an attempt to lessen flexion of a forceps operating wire extending from the forceps through a guide sleeve to the outside, whereby a progressive and recessive motion of the forceps per se may be readily and independently controlled, an orientational approach of the forceps toward a target spot of tissues may be finely and delicately controlled, and when taking a sample tissue, the forceps would not move unstably in any direction. This invention is essentially directed to meet such requirements.

SUMMARY OF THE INVENTION

It is therefore a primary object of the present invention to provide an improved biopsical fiber scope having a pair of forceps incorporated and controllable by a single operator wherein there is provided adaptor means at or adjacent to an inlet of a forceps guide sleeve which is adapted to controllably guide the direction of the travel of a forceps controlling wire within the guide sleeve.

It is another object of this invention to provide an improved biopsical fiber scope having a pair of forceps incorporated and controllable by a single operator wherein there is provided adaptor means at an inlet of a forceps guide sleeve which is adapted to prevent a flexion of a forceps controlling wire within a forceps guide sleeve.

It is still another object of this invention to provide an improved biopsical fiber scope controllable by a single operator and enabling a precise and fine control in the orientational approach toward a target spot of tissue while manually operating a pair of forceps.

According to this invention, briefly summarized by way of a preferred embodiment thereof, there is provided an improved biopsical fiber scope controllably manipulated by a single operator wherein there is provided a pair of biopsy forceps, and a stopper adapted to fix the biopsy forceps with respect to the body of a fiber scope is provided on an appropriate position of adaptor means.

According to another embodiment of this invention, there is provided an improved biopsical fiber scope controllable by a single operator wherein there is provided a pair of biopsy forceps, and a stopper adapted to fix the biopsy forceps both translationally and rotationally with respect to the fiber scope proper is provided at a desired position on a forceps controlling wire guide sleeve which is connected at its one end to adaptor means.

The foregoing objects, characteristics, principle and details of the present invention, as well as further objects and advantages thereof, will become apparent from the following detailed description with respect to preferred embodiments of the invention when read in conjunction with the accompanying drawings, in which like parts are designated with like reference numerals.

DETAILED DESCRIPTION OF THE PREFERRED EMBODIMENTS

Figure 1:
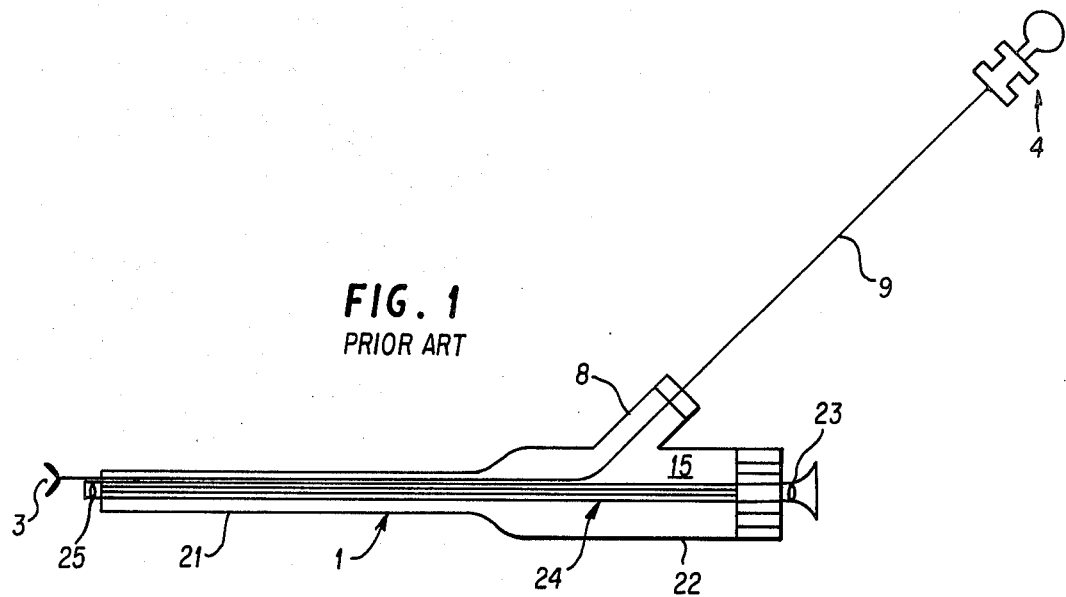
FIG. 1 is a general schematic view showing a biopsical fiber scope according to a prior art.

The construction and operation of an improved biopsical fiber scope according to this invention will now be described in detail with respect to preferred embodiments thereof by referring to the accompanying drawings. It should be understood, however, that the embodiments appeared herein are for illustrative purpose only, but not in any way for limiting the scope and spirit of the invention.

Before proceeding further, it will be convenient to fully understand the characteristic features of the operation of a biopsical fiber scope having a pair of forceps for taking a sample from a designated part of tissue in an internal organ.

When operating a biopsical fiber scope by a single operator for biopsy use, it is necessary for an operator to handle the body or control unit housing 22 of a fiber scope with one hand while observing the interior of an internal organ through an optic assembly of the fiber scope including an eyepiece assembly, the bundle of optical fibers and an objective assembly, and operate a forceps through a controlling wire with the other hand. However, since a biopsical fiber scope of the conventional construction is designed for use with two operators, or one operator and an assistant, a forceps controlling wire extends longitudinally from a guide sleeve of the fiber scope towards the two opposite exterior portions.

In order for a single operator to carry out biopsical examination, it is first necessary to shorten the extension or length of a forceps controlling wire to a suitable extent, as too long an extension of the controlling wire is not practicable for single operator use. However, if the forceps controlling wire only is cut short to a desired length, it becomes practicably difficult to handle or even impossible to control a travelling motion of the forceps while making observation through the finder of the fiber scope, as the controlling wire is now unstable in its orientational positioning at the inlet of the wire guide sleeve. In more detail, the forceps controlling wire comprises a thin control steel wire and a plurality of metal wires wound spirally around the central steel wire, so that the controlling wire may provide a resilient and flexible property. Consequently, such construction of the controlling wire would likely prevent smoothness in its progressive or recessive motion in sliding at the inlet of the wire guide sleeve, thus possibly resulting is a flexion in the wire at the inlet of the guide sleeve.

According to the present invention, there is provided suitable adaptor means at the inlet portion of the forceps controlling wire guide sleeve, whereby it is now possible to direct a progressive motion or a recessive motion of the forceps controlling wire into or out of the guide sleeve and prevent a flexion of the wire from occurring, thus allowing an easy control of the directional motion in sliding of the forceps controlling wire through the inlet of the guide sleeve. For this purpose, there is provided a thin path of a desired extension (which varies according to the type of fiber scope) through which the forceps controling wire is threaded and in a given direction at the inlet of the guide sleeve of the biopsical fiber scope. For the material of the adaptor means designed for the purpose mentioned above, any of such material may be used such as a synthetic plastic resin, a metal, etc. By using such adaptor means, a controllability of a biopsical fiber scope by a single operator is greatly improved. A biopsical examination by using the fiber scope according to this invention may extensively be applied to a further similar operation such as a polypectomy, etc.

Description on the construction of an improved biopsical fiber scope according to this invention will now be made in detail with respect to preferred embodients thereof in conjunction with the accompanying drawings.

Figure 2:
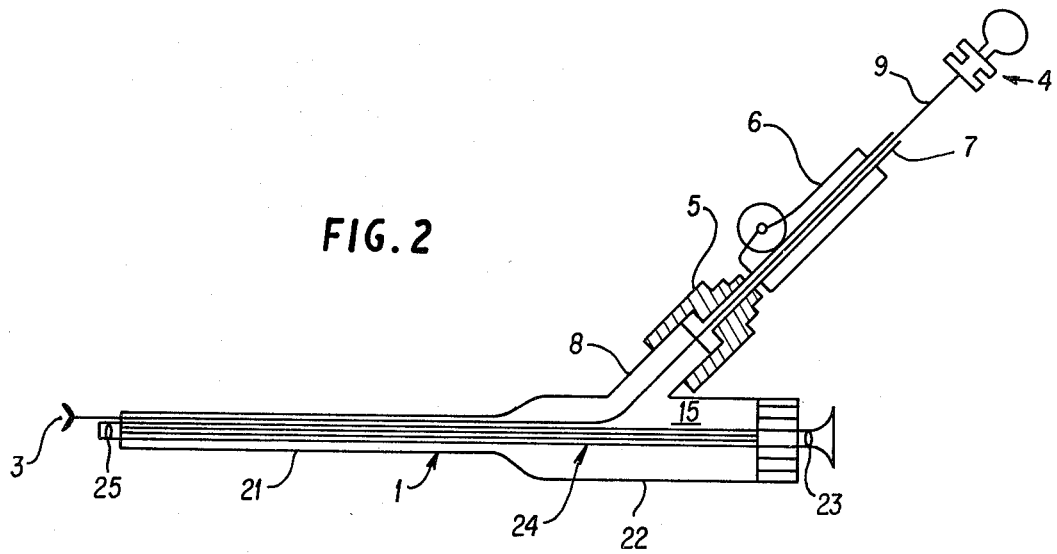
FIG. 2 is a general schematic view showing a biopsical fiber scope according to this invention.

Referring now to FIG. 2, there is shown an adaptor 5 at the inlet to a guide sleeve 8 of the fiber scope 1. The guide sleeve 8 forms a portion of the control unit housing 22 which has therein a branched conduit 15. As described later in detail in connection with FIG. 3, the adaptor is formed of a hard plastic resin, metal or the like, and is fitted on the outer circumference of a guide sleeve 8 for a forceps controlling wire 9, to which connected is one end of a flexible tube 7 made a thin plastics such as polyvinyl chloride or a tube braided of a plurality of thin metal wires for covering the forceps controlling wire 9. The above mentioned flexible tube 7 can be emitted in the practice of this flexible invention, but with use of this tube 7, a biopsical operation can advantageously be performed with greater ease. The length of the adaptor 5 is designed for an extension which may positively direct the sliding motion of the forceps controlling wire 9, and which may vary depend on the type of a biopsical fiber scope. The connection between the adaptor 5 and the forceps guide sleeve 8 may be obtained preferably by a threaded connection means therebetween. In the embodiment shown in FIG. 3, the flexible tube 7 received within the adaptor is further extended toward the neck of the forceps control means or operating handle 4 to cover the forceps controlling wire 9, and there is further disposed a stopper 6 in the proximity of the adaptor 5 mounted on the flexible tube 7. The stopper 6 may be of a similar type to that applicable to an adjuster means for an instillation liquid as in use of the ease of instillation. In detail, when a central shaft of a roll 11 is moved along a sliding groove 12, at one end of the groove 12 the roll 11 may urge the forceps controlling wire 9 within the stopper 6 with respect to the flexible tube 7, while at the other end thereof where the above mentioned groove 12 is made larger, the forceps controlling wire 9 can be relieved from an engagement or urging action against the flexible tube 7.

Figure 4:
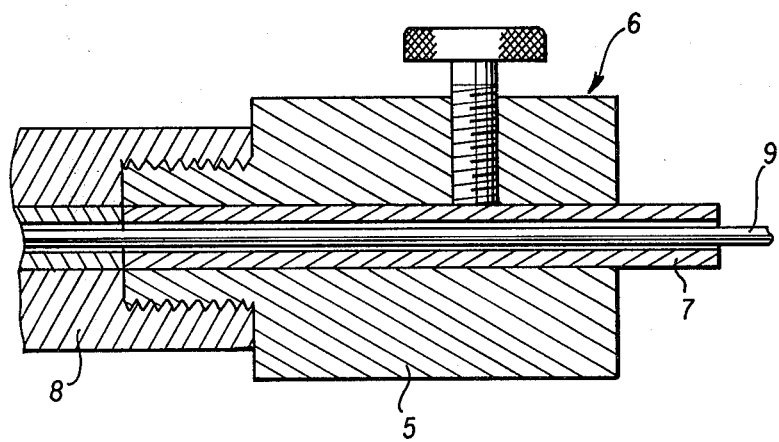
FIG. 4 is a similar view to FIG. 3 showing a modification of an adaptor and a stopper for use in a fiber scope.

Now referring to FIG. 4, there is shown another embodiment of the adaptor according to this invention, wherein the adaptor 5 is threadedly connected with the inside of the forceps guide sleeve 8 of the control unit housing 22 at the inlet thereof, and there is provided the stopper 6 in a desired position on the adaptor 5. The stopper 6 is provided with threads and is adapted to threadedly progress, when screwed-in, into the adaptor 5 so as to urge the forceps controlling wire 9 through the flexible tube 7 against the adaptor 5, thus functioning to prevent the forceps 3 from moving in any way.

Figure 3:
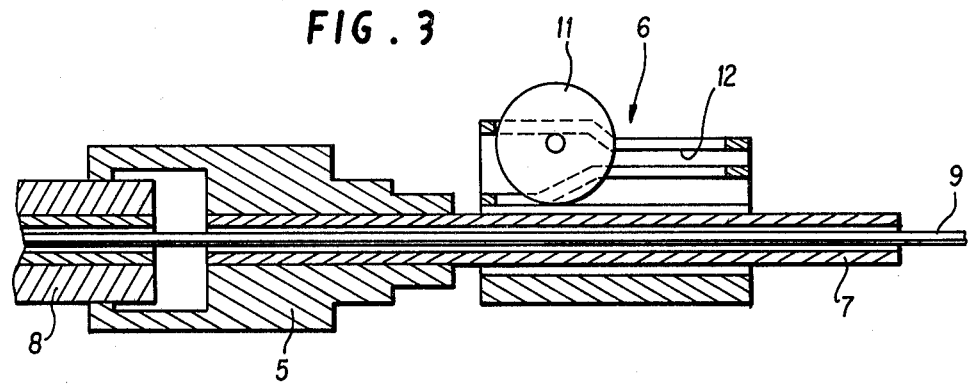
FIG. 3 is an enlarged fragmentary cross-sectional view showing an adaptor and a stopper shown in FIG. 2.

Incidentally, the flexible tube 7 as shown connected to the inside of the adaptor 5 in FIGS. 3 and 4 may not be connected so far, but may be connected at the end area, for instance, of the adaptor. On the other hand, when the adaptor 5 and the flexible tube 7 are made of the same material, it is also possible to form them in an integral construction.

In operation, a single operator can conduct a biopsical examination and sampling procedures in such a manner that while making observation therefor of the interior of an internal organ of a patient through the optic assembly including the eyepiece assembly 23, the optical fiber bundle 24, and the objective assembly 25, and holding with one hand the control unit housing 22 and operating the distal end of the flexible hollow conduit portion 21 of the fiber scope with an accurate and appropriate orientational control by using a control means (not shown) at the head of the control unit housing 22 so as to approach to a target focus spot in the living organ, it is now possible for him to handle the forceps 3 by adjusting the degree of extension thereof with the other hand. In general, the orientational control for the purpose of orientating and pointing the tip ends of the forceps 3 at a target spot in the organ has usually been difficult to perform precisely, since the fiber scope per se has a substantial flexibility, furthermore the internal organ also may move peristaltically during the fiber scope operation.

In this respect, according to this invention there is specifically provided a stopper 6 which is adapted to selectively fix the extension of the forceps 3 within the interior of the organ in order to perform such orientational control finely and precisely. The stopper 6 is operated in such a manner that it is threadedly secured for fixing the extension of the forceps 3 on one hand, while it is unscrewed to release the forceps 3 on the other, whereby the orientational control of the forceps 3 may be effected with a delicate and versatile operability. In this respect, it is preferred that the stopper 6 is of a construction permitting an easy adjustment so that it may be controlled quickly whenever so required. The location of the stopper 6 is preferably at a suitable position for ready accessibility on the flexible tube 7 covering the forceps controlling wire.

As fully described hereinbefore, this invention provides an improved biopsical fiber scope which is operable with a single operator, with ease of handling, and which can advantageously afford a quick and precise sampling action in its biopsical use in the interior of an internal organ of a patient.

Although detailed descriptions have been made exclusively on the foregoing typical embodiments of this invention, it should be understood, as indicated hereinbefore, that the preferred embodiments as described and shown herein do not mean in any way limitations of this invention thereto, but on the contrary, many changes, variations and modifications with respect to the construction and arrangement in practice thereof may further be derived by those skilled in the art to which the present invention pertains, whereby the advantageous characteristics of this invention may be realized without departing from the spirit and scope of the invention as set forth hereunto in the appended claims.

What is claimed is:

1. A fiberoptic endoscope comprising:
   a control unit housing;
   a branched conduit in said housing having a first proximal end, a second proximal end and a distal end, said first proximal end having an inlet opening;
   a flexible hollow conduit attached to said housing having a proximal end and a distal end, the proximal end being fixed in said housing at the distal end of said branched conduit and extending from said distal end of said branched conduit;
   an optic assembly comprising an eyepiece assembly mounted in said housing at said second proximal end, a bundle of flexible optical fibers extending in said branched conduit and said hollow conduit from said eyepiece assembly to said distal end of said hollow conduit, and an objective assembly mounted on said distal end of said hollow conduit optically connected through said bundle of optical fibers to said eyepiece assembly;
   a guide sleeve formed as a portion of said housing at said inlet opening of said first proximal end of said branched conduit;
   a flexible tube operatively aligned with said guide sleeve and said inlet opening;
   a flexible forceps control wire extendable and retractable through said flexible tube, said guide sleeve, said inlet opening, said hollow conduit to and beyond the distal end and from the entirety thereof;
   a forceps attached to said flexible forceps control wire at an end of said wire extending beyond the distal end of said hollow conduit, said forceps being at all times during observation and tissue taking in controllable view of said optic assembly;
   a forceps control means attached to said forceps control wire at the other end of said wire extending out of said flexible tube; and
   an adaptor holding said flexible tube to said guide sleeve and defining a narrow path with said flexible tube from said inlet opening extending outwardly in the direction of said forceps control means for slidably guiding said forceps control wire in combination with said flexible tube, said adaptor providing said narrow path for a length sufficient to positively support said flexible tube and the flexible tube being of sufficient length to positively direct the sliding motion of said forceps control wire, said flexible tube being connected to said adaptor, said forceps control wire being of such a length that the portion of wire between said adaptor and said forceps control means can, at all times, be maintained in longitudinal extension without flexion during progressive and recessive motion to and from a target spot of tissue, and an entire biopsy operation including a final operation of taking a tissue sample can be performed by a single operator by controlling said forceps control means in one hand and holding said control unit housing in said operator's other hand.

2. An improved fiberoptic endoscope according to claim 1 further comprising:
   stopper means mounted on said flexible tube for selectively fixing the longitudinal and rotational motion of said forceps control wire.

3. Performing a polypectomy using the fiberoptic endoscope as claimed in either claim 1 or 2.

* * * * *